United States Patent [19]

Renth et al.

[11] 4,094,980
[45] June 13, 1978

[54] N-[1-(3',4'-METHYLENEDIOXY-PHENYL)-PROPYL-(2)]-N'-PHENYL-PIPERAZINES AND SALTS THEREOF

[75] Inventors: Ernst-Otto Renth; Anton Mentrup; Kurt Schromm; Wilhelm Frölke, all of Ingelheim am Rhein, Germany

[73] Assignee: Boehringer Ingelheim GmbH, Ingelheim am Rhein, Germany

[21] Appl. No.: 749,344

[22] Filed: Dec. 10, 1976

Related U.S. Application Data

[63] Continuation-in-part of Ser. No. 608,455, Aug. 28, 1975, abandoned.

[30] Foreign Application Priority Data

Sep. 3, 1974 Germany .............................. 2442158

[51] Int. Cl.² .................. A61K 31/495; C07D 295/08
[52] U.S. Cl. ..................................... 424/250; 544/377; 544/395
[58] Field of Search ................. 260/268 BC; 424/250

[56]  References Cited

U.S. PATENT DOCUMENTS 3,729,474  4/1973  Mentrup et al. .............. 260/268 BC Primary Examiner—Paul M. Coughlan, Jr.
Attorney, Agent, or Firm—Hammond & Littell

[57] ABSTRACT

Compounds of the formula

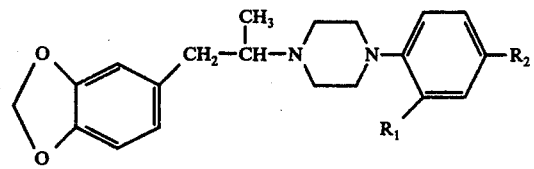

wherein
  $R_1$ and $R_2$ are chlorine, or
  $R_1$ is methyl and $R_2$ is methoxy, and non-toxic, pharmacologically acceptable acid addition salts thereof; the compounds as well as their salts are useful as anti-hyperlipidemics and anti-hypercholesteremics with practically negligible CNS-depressing side effects.

5 Claims, No Drawings

N-[1-(3',4'-METHYLENEDIOXY-PHENYL)-PROPYL-(2)]-N'-PHENYL-PIPERAZINES AND SALTS THEREOF

This is a continuation-in-part or copending application Ser. No. 608,455 filed Aug. 28, 1975, now abandoned.

This invention relates to novel N-[1-(3',4'-methylenedioxy-phenyl)-propyl-(2)]-N'-phenyl-piperazines and non-toxic, pharmacologically acceptable acid addition salts thereof, as well as to a method of preparing these compounds.

THE PRIOR ART

German Offenlegungsschrift No. 1,670,144 and U.S. Pat. No. 3,729,474 disclose a genus of N-(1-aryl-propyl-2)-N'-phenyl-piperazines represented by the formula

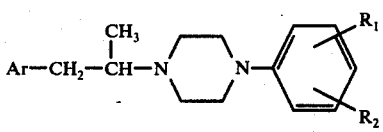

wherein
Ar is an aromatic bicyclic fused-ring radical, where the ring not directly attached to the 1,2-propylene moiety may be an isocyclic or heterocyclic saturated or aromatic ring, and
$R_1$ and $R_2$ are each hydrogen, halogen, trifluoromethyl, alkyl of 1 to 4 carbon atoms or alkoxy of 1 to 4 carbon atoms,
and non-toxic acid addition salts thereof; these compounds are disclosed to be useful as CNS-depressants. The prior art does not disclose, however, any species where Ar is 3,4-methylenedioxy-phenyl, $R_1$ and $R_2$ are chlorine, or $R_1$ is methyl and $R_2$ is methoxy.

THE INVENTION

We have now discovered that a novel selective subgeneric class of compounds not specifically disclosed in the prior art, namely compounds of the formula

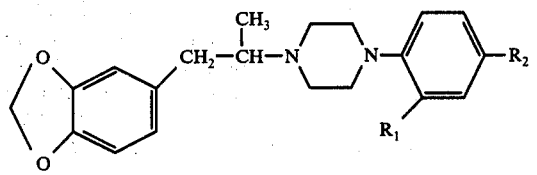

wherein
$R_1$ and $R_2$ are chlorine, or
$R_1$ is methyl and $R_2$ is methoxy,
and non-toxic, pharmacologically acceptable acid addition salts thereof, not only exhibit extraordinarily effective anti-hyperlipidemic and anti-hypercholesteremic activities which are significantly superior to those of the compounds disclosed in German Offenlegungsschrift No. 2,136,929, but also virtually negligible CNS-depressing side effects.

The compounds embraced by formula I above may be prepared by the following method, inter alia:

By reacting an N-phenyl-piperazine of the formula

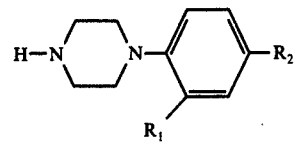

wherein $R_1$ and $R_2$ have the same meanings as in formula I, with a compound of the formula $$
\begin{array}{c}
\text{(III)}
\end{array}
$$

wherein X is an electrophilic substituent, such as chlorine, bromine, methanesulfonyl, p-toluene-sulfonyl or the like, in the presence of an acid-binding agent.

The starting compounds of the formula II are readily accessible by known methods, for example by the process described in J.A.C.S. 76, 1853 (1954), or by the process disclosed in J. Med. Chem. 8, 332 (1965).

The electrophilic compounds of the formula III may be obtained by esterification of 1-(3',4'-methylenedioxyphenyl)-propanol-(2) with the corresponding acid halide (see Example 1).

The compounds of the formula I comprise an asymmetric carbon atom in the —CH(CH$_3$)— grouping and, accordingly, occur in the form of racemates as well as optically active antipodes. The optically active compounds may be obtained either by using the corresponding optically active starting compound III, or by converting a racemate of a compound of the formula I into a diastereo-salt thereof with the aid of an optically active auxiliary acid, such as dibenzoyl-D-tartaric acid or D-3-bromo-camphor-8-sulfonic acid, and separating the optically active components by fractional precipitation or fractional crystallization, pursuant to conventional procedures.

The compounds embraced by formula I are organic bases and therefore form acid addition salts with inorganic or organic acids. Examples of non-toxic, pharmacologically acceptable acid addition salts are those formed with hydrochloric acid, hydrobromic acid, sulfuric acid, methanesulfonic acid, succinic acid, tartaric acid, 8-chlorotheophylline or the like.

The following examples illustrate the present invention and will enable others skilled in the art to understand it more completely. It should be understood, however, that the invention is not limited solely to the particular examples given below.

EXAMPLE 1

N-[1-(3',4'-Methylenedioxy-phenyl)-propyl-(2)]-N'-(o-methyl-p-methoxy-phenyl)-piperazine and its hydrochloride A mixture consisting of 29.0 gm (0.14 mol) of N-(2-methyl-4-methoxy-phenyl)-piperazine, 41.5 gm (0.16 mol) of 1-(3',4'-methylenedioxy-phenyl)-propanol-(2) methanesulfonate (prepared by esterification of the free propanol with methanesulfonyl chloride), 44 gm of anhydrous potash and 250 ml of xylene was refluxed for seven hours. Thereafter, the xylene was distilled off in vacuo, and the residue, i.e. the raw free base reaction product, was recrystallized from aqueousmethanolic hydrochloric acid, yielding the hydrochloride of the formula

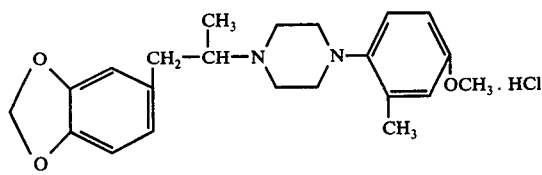

which had a melting point of 256°–259° C.

EXAMPLE 2

Using a procedure analogous to that described in Example 1, N-[1-(3',4'-methylenedioxy-phenyl)-propyl-(2)]-N'-(o,p-dichloro-phenyl)-piperazine and its hydrochloride, m.p. 259°–263° C, of the formula

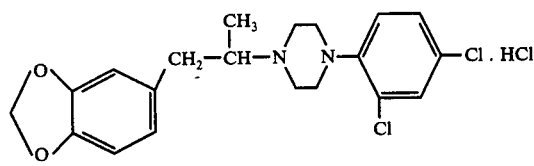

were prepared from 32.5 gm (0.14 mol) of N-(2,4-dichlorophenyl)-piperazine and 41.5 gm (0.16 mol) of 1-(3',4'-methylenedioxy-phenyl)-propanol-(2) methanesulfonate in the presence of 44 gm of anhydrous potash in 250 ml of xylene.

The compounds of the present invention, that is, the racemic or optically active compounds of the formula I, and non-toxic, pharmacologically acid addition salts thereof, have the useful pharmacodynamic properties previously described above.

The anti-hypercholesteremic and CNS-depressing activities of the compounds of this invention and of closely related compounds disclosed in the prior art were ascertained by the methods described below, and the tables show the results obtained, where A = N-[1-(3,4-methylenedioxy-phenyl)-propyl-(2)]-N'-(2,4-dichloro-phenyl)-piperazine, described in Example 2 above;

B = N-[1-(3,4-methylenedioxy-phenyl)-propyl(2)]-N'-(2-methyl-4-methoxy-phenyl)-piperazine, described in Example 1 above;

C = N-[1-(3,4-methylenedioxy-phenyl)-propyl(2)]-N'-(2-chlorophenyl)-piperazine, disclosed in Example 18 of U.S. Pat. No. 3,729,474;

D = N-[1-(3,4-methylenedioxy-phenyl)-propyl(2)-N'-(2-methoxy -phenyl)-piperazine, disclosed in Example 3 of U.S. Pat. No. 3,729,474; and E = N-[1-(3,4-methylenedioxy-phenyl)-propyl(2)]-N'-(2,6-dimethyl-phenyl)-piperazine, disclosed in Example 2 of U.S. Pat. No. 3,729,474.

1. Reduction of serum cholesterol level

Test Animals 85 male laboratory rats having a body weight of about 250 gm. The animals were individually kept in Makrolon-cages under controlled conditions. Food and water were freely accessible to the animals at all times, except on the day on which the blood samples were taken.

Administration

The test compounds were administered once daily per os by means of an esophageal sound.

Dosage and Number of Animals

| Compound | Dose mgm/kg | No. of animals |
|---|---|---|
| Physiol. NaCl sol. | Control | 15 |
| A | 25 | 10 |
| B | 25 | 10 |
| C | 25 | 10 |
| D | 50 | 15 |
| E | 50 | 15 |

Duration of Test 3 weeks

Analytical Method

Determination of total cholesterol in serum (mgm/100 ml) with the auto-analyzer according to Liebermann-Burchard (see J. Levine et al, Technicon-Symposium, 1967, Vol. 1, pg. 25).

Time of Determination

The total serum cholesterol was determined in all test animals prior to the beginning of the test (day O), as well as on the 8th, 14th and 21st day. The blood sample was taken from the retrobulbar venous plexus. The animals were fasted for about 16 hours prior to determination of the serum cholesterol.

TABLE I

| | Average value of total serum cholesterol (mgm/100 ml) | | | | | |
|---|---|---|---|---|---|---|
| | | Invention | | Prior art | | |
| Compound | | Controls | A | B | C | D | E |
| Day 0 | $\bar{x}$ | 110.3 | 96.7 | 97.9 | 38.3 | 112.9 | 107.3 |
| | s | 9.7 | 19.4 | 16.0 | 13.1 | 20.2 | 16.5 |
| Day 8 | $\bar{x}$ | 101.8 | 27.5 | 35.2 | 31.7 | 87.3 | 71.2 |
| | s | 12.7 | 7.2 | 6.7 | 7.5 | 19.7 | 15.4 |
| Day 14 | $\bar{x}$ | 97.1 | 12.5 | 21.3 | 24.3 | 86.3 | 61.7 |
| | s | 8.6 | 1.6 | 5.4 | 8.9 | 16.1 | 20.1 |
| Day 21 | $\bar{x}$ | 101.6 | 13.0 | 21.2 | 26.2 | 82.1 | 63.5 |
| | s | 10.3 | 2.9 | 6.0 | 10.0 | 17.4 | 34.2 |

$\bar{x}$ = Average group value
s = Standard deviation

2. CNS-Depression (a) Sliding test

A statistically significant number of adult laboratory mice of the NMRI-strain are used as test animals. The test compound is administered perorally as a suspension in tylose by means of an esophageal sound, and the animal is placed on an inclined plate of glass. If the administered dose of the test compound has a CHS-depressing effect upon the animal, the treated mouse loses its normal holding reflex and slides off the plate. The test is repeated at varying dosage levels, and a median effective dose ($ED_{50}$) is determined by the so-called Probit-method, i.e. the dose at which 50% of the test animals begin to slide off the glass plate.

(b) Ataxia

A statistically significant number of adult laboratory mice of the NMRI-strain are used as the test animals. The test compound is administered perorally as a suspension in tylose by means of an esophageal sound, and the treated animal is observed for evidence of atactic (uncoordinated) walking. The test is repeated at varying dosage levels, and a median effective dose ($ED_{50}$) is determined by the Probit-method, i.e. the dose at which ataxia occurs in 50% of the animals.

TABLE II

| Compound | Sliding test $ED_{50}$ mgm/kg p.o. | Ataxia $ED_{50}$ mgm/kg p.o. |
|---|---|---|
| Application: | | |
| A | 190 | 160 |
| B | 960 | 120 |
| Prior Art: | | |
| C | 2.2 | 2.2 |
| D | >14 | 39 |
| E | 25 | 105 |

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

Tablets

The tablet composition is compounded from the following ingredients:

| | | |
|---|---|---|
| N-[1-(3',4'-methylenedioxy-phenyl)-propyl-(2)]-N'-(o,p-dichloro-phenyl)-piperazine hydrochloride | 50 | parts |
| Lactose | 50 | " |
| Corn starch | 93 | " |
| Secondary calcium phosphate | 47 | " |
| Soluble starch | 3 | " |
| Magnesium stearate | 3 | " |
| Colloidal silicic acid | 4 | " |
| Total | 250 | parts |

Preparation

The piperazine compound, the lactose, the corn starch and the calcium phosphate are intimately admixed with each other, the mixture is moistened with an aqueous solution of the soluble starch, the moist mass is granulated through a fine-mesh screen, the granulate is dried, the dry granulate is admixed with the magnesium stearate and the colloidal silicic acid, and the resulting composition in compressed into 250 mgm-tablets in a conventional tablet making machine. Each tablet contains 50 mgm of the piperazine compound and is an oral dosage unit composition with effective anti-hyperlipidemic and anti-hypercholesteremic action.

EXAMPLE 4

Coated pills

The pill core composition is compounded from the following ingredients:

| | | |
|---|---|---|
| N-[1-(3',4'-methylenedioxy-phenyl)-N'-(o-methyl-p-methoxy-phenyl)-piperazine hydrochloride | 40 | parts |
| 2,6-Bis-(diethanolamino)-4,8-dipiperidino-pyrimido[5,4-d]-pyrimidine | 70 | " |
| Corn starch | 60 | " |
| Secondary calcium phosphate | 50 | " |
| Soluble starch | 3 | " |
| Magnesium stearate | 3 | " |
| Colloidal silicic acid | 4 | " |
| Total | 230 | parts |

Preparation

The ingredients are compounded in a manner analogous to the tablet composition of the preceding example, and the composition is compressed into 230 mgm-pill cores, which are subsequently coated with a thin shell consisting essentially of a mixture of sugar, talcum and gum arabic. Each of the resulting coated pills contains 40 mgm of piperazine compound and 70 mgm of the pyrimidopyrimidine compound, and is an oral dosage unit composition with effective anti-hyperlipidemic, anti-hypercholesteremic and coronary vasodilating actions.

EXAMPLE 5

Gelatin Capsules

The capsule filler composition is compounded from the following ingredients:

| | | |
|---|---|---|
| N-[1-(3',4'-methylenedioxy-phenyl)-propyl-(2)]-N'-(o,p-dichloro-phenyl)-piperazine hydrochloride | 60 | parts |
| Inert solid diluent (e.g. starch, lactose or kaolin) | 240 | " |
| Total | 300 | parts |

Preparation

The ingredients are intimately admixed, the mixture is milled into homogeneous dry powder, and 300 mgm-portions of the powder are filled into gelatin capsules of suitable size. Each capsule contains 60 mgm of the piperazine compound and is an oral dosage unit composition with effective anti-hyperlipidemic and anti-hypercholesteremic action.

Analogous results were obtained when any one of the other piperazine compounds embraced by formula I or a non-toxic acid addition salt thereof was substituted for the particular piperazine compound in Examples 3 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

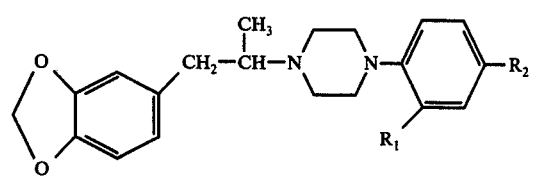

wherein $R_1$ and $R_2$ are chlorine, or $R_1$ is methyl and $R_2$ is methoxy, or a non-toxic, pharmacologically acceptable acid addition salt thereof.

2. A compound of claim 1, which is N-[1-(3',4'-methylenedioxy-phenyl)-propyl)-(2)]-N'-(o,p-dichloro-phenyl)-piperazine or a non-toxic, pharmacologically acceptable acid addition salt thereof.

3. A compound of claim 1, which is N-[1-(3',4'-methylenedioxy-phenyl)-propyl-(2)]-N'-(o-methyl-p-methoxy-phenyl)-piperazine or a non-toxic, pharmacologically acceptable acid addition salt thereof.

4. A pharmaceutical dosage unit composition consisting essentially of an inert pharmaceutical carrier and an effective anti-hyperlipidemic or anti-hypercholesteremic amount of a compound of claim 1.

5. The method of lowering the blood fat level or lowering the serum cholesterol level in a warm-blooded animal in need of such treatment, which comprises adminstering to said animal an effective anti-hyperlipidemic or anti-hypercholesteremic amount of a compound of claim 1.

* * * * *

UNITED STATES PATENT OFFICE
CERTIFICATE OF CORRECTION

Patent No. 4,094,980             Dated June 13, 1978

Inventor(s) ERNST-OTTO RENTH, ANTON MENTRUP, KURT SCHROMM and WILHELM FROLKE

It is certified that error appears in the above-identified patent and that said Letters Patent are hereby corrected as shown below:

Col. 1, line 5, correct "or copending" to read --of copending--.

Col. 4, line 37, in Table 1, first entry under column "C", correct "38.3" to read --88.3--;

line 53, correct "CHS" to read --CNS--

Signed and Sealed this

Twenty-eighth Day of November 1978

[SEAL]

Attest:

RUTH C. MASON
Attesting Officer

DONALD W. BANNER
Commissioner of Patents and Trademarks